US010388945B2

(12) United States Patent
Nishide et al.

(10) Patent No.: US 10,388,945 B2
(45) Date of Patent: Aug. 20, 2019

(54) NON-AQUEOUS ELECTROLYTE SECONDARY BATTERY

(71) Applicant: Sanyo Electric Co., Ltd., Daito-shi, Osaka (JP)

(72) Inventors: Daisuke Nishide, Hyogo (JP); Atsushi Fukui, Hyogo (JP)

(73) Assignee: SANYO Electric Co., Ltd., Osaka (JP)

( * ) Notice: Subject to any disclaimer, the term of this patent is extended or adjusted under 35 U.S.C. 154(b) by 0 days.

(21) Appl. No.: 15/523,994

(22) PCT Filed: Nov. 20, 2015

(86) PCT No.: PCT/JP2015/005802
§ 371 (c)(1),
(2) Date: May 3, 2017

(87) PCT Pub. No.: WO2016/084357
PCT Pub. Date: Jun. 2, 2016

(65) Prior Publication Data
US 2017/0338466 A1    Nov. 23, 2017

(30) Foreign Application Priority Data

Nov. 28, 2014   (JP) ................. 2014-240849

(51) Int. Cl.
| | |
|---|---|
| *H01M 4/131* | (2010.01) |
| *H01M 4/505* | (2010.01) |
| *H01M 4/525* | (2010.01) |
| *H01M 10/0567* | (2010.01) |
| *C01B 25/30* | (2006.01) |
| *H01M 10/0525* | (2010.01) |
| *H01M 4/36* | (2006.01) |
| *H01M 4/62* | (2006.01) |
| *C07C 69/24* | (2006.01) |

(52) U.S. Cl.
CPC ............. *H01M 4/131* (2013.01); *C01B 25/30* (2013.01); *H01M 4/364* (2013.01); *H01M 4/505* (2013.01); *H01M 4/525* (2013.01); *H01M 4/62* (2013.01); *H01M 10/0525* (2013.01); *H01M 10/0567* (2013.01); *C07C 69/24* (2013.01); *Y02E 60/122* (2013.01); *Y02T 10/7011* (2013.01)

(58) Field of Classification Search
None
See application file for complete search history.

(56) References Cited

U.S. PATENT DOCUMENTS

| 8,012,625 B2 | 9/2011 | Yamamoto et al. | |
|---|---|---|---|
| 2008/0063941 A1* | 3/2008 | Itaya ................. | H01M 4/13 429/231.95 |
| 2008/0131781 A1 | 6/2008 | Yong et al. | |
| 2010/0015514 A1 | 1/2010 | Miyagi et al. | |
| 2011/0217598 A1 | 9/2011 | Kawashima et al. | |
| 2011/0223489 A1 | 9/2011 | Iwanaga et al. | |
| 2013/0101900 A1* | 4/2013 | Nagai ................. | H01M 4/525 429/223 |
| 2013/0309570 A1* | 11/2013 | Kim ................. | H01M 4/505 429/213 |
| 2014/0138591 A1* | 5/2014 | Yoon ................. | C01B 25/45 252/519.14 |
| 2016/0294008 A1* | 10/2016 | Yoshida ............ | H01M 10/0525 |

FOREIGN PATENT DOCUMENTS

| CN | 101292389 A | 10/2008 |
|---|---|---|
| CN | 102195088 A | 9/2011 |
| JP | 5-74490 A | 3/1993 |
| JP | 2006-252895 A | 9/2006 |
| JP | 2008-123972 A | 5/2008 |
| JP | 2011-192536 A | 9/2011 |
| WO | 2006/019245 A1 | 2/2006 |

OTHER PUBLICATIONS

International Search Report dated Feb. 2, 2016, issued in counterpart International Application No. PCT/JP2015/005802 (2 pages).
Search Report dated Oct. 31, 2018, issued in counterpart Chinese application No. 201580064436.X, with English translation. (2 pages).

* cited by examiner

*Primary Examiner* — Alix E Eggerding
(74) *Attorney, Agent, or Firm* — Westerman, Hattori, Daniels & Adrian, LLP

(57) ABSTRACT

A nonaqueous electrolyte secondary battery includes a positive electrode including a positive electrode mix layer, a negative electrode, and a nonaqueous electrolyte. The positive electrode mix layer contains a lithium transition metal oxide containing zirconium (Zr) and also contains a phosphate compound. The nonaqueous electrolyte contains a linear carboxylate. According to this configuration, the nonaqueous electrolyte secondary battery, which has excellent low-temperature output characteristics, can be provided. Thus, the nonaqueous electrolyte secondary battery is, for example, a power supply for driving a mobile data terminal such as a mobile phone, a notebook personal computer, a smartphone, or a tablet terminal and is particularly suitable for applications needing high energy density. Furthermore, the nonaqueous electrolyte secondary battery is conceivably used for high-output applications such as electric vehicles (EVs), hybrid electric vehicles (HEVs), and electric tools.

11 Claims, No Drawings

NON-AQUEOUS ELECTROLYTE SECONDARY BATTERY

TECHNICAL FIELD

The present disclosure relates to a nonaqueous electrolyte secondary battery.

BACKGROUND ART

Patent Literature 1 proposes that a solvent mixture of ethylene carbonate and methyl propionate is used as a solvent for nonaqueous electrolyte solutions for the purpose of improving cycle characteristics and low-temperature load characteristics of a nonaqueous electrolyte secondary battery. Patent Literature 2 proposes a positive electrode containing inorganic particles having lithium transferability for the purpose of increasing the safety of lithium secondary batteries during overcharge or the like.

CITATION LIST

Patent Literature

PTL 1: Japanese Published Unexamined Patent Application No. 5-74490
PTL 2: WO 2006-019245

SUMMARY OF INVENTION

Technical Problem

Incidentally, it is important that nonaqueous electrolyte secondary batteries have excellent output characteristics in low-temperature environments mainly for applications for, for example, motor power supplies for electric vehicles (EVs), hybrid electric vehicles (HEVs), electric tools, and the like. However, it is difficult to obtain sufficient low-temperature output characteristics by techniques including Patent Literatures 1 and 2. Improvements in low-temperature output characteristics are required.

Solution to Problem

A nonaqueous electrolyte secondary battery according to one embodiment of the present disclosure includes a positive electrode including a positive electrode mix layer, a negative electrode, and a nonaqueous electrolyte. The positive electrode mix layer contains a lithium transition metal oxide containing zirconium (Zr) and also contains a phosphate compound. The nonaqueous electrolyte contains a linear carboxylate.

Advantageous Effects of Invention

According to one embodiment of the present disclosure, a nonaqueous electrolyte secondary battery having excellent low-temperature output characteristics can be provided.

DESCRIPTION OF EMBODIMENTS

In a nonaqueous electrolyte secondary battery according to one embodiment of the present disclosure, a positive electrode mix layer contains a lithium transition metal oxide containing zirconium (Zr) and also contains a phosphate compound and a nonaqueous electrolyte contains a linear carboxylate. In accordance with the nonaqueous electrolyte secondary battery according to one embodiment of the present disclosure, a good (low-resistance) coating is formed on the surface of the Zr-containing lithium transition metal oxide, which is a positive electrode active material. This probably reduces, for example, reaction resistance on the surface of an active material to enhance low-temperature output characteristics. The inventors have succeeded in increasing the reactivity between an active material and solvent molecules in the nonaqueous electrolyte by allowing the lithium transition metal oxide to contain Zr and also have succeeded in reducing the resistance of a coating formed on the active material surface by the degradation of the solvent molecules by allowing the phosphate compound to be present near the active material surface. Such a low-resistance coating is probably formed only in the case where the linear carboxylate is used as a nonaqueous solvent, the lithium transition metal oxide contains Zr, and the phosphate compound is present near the active material surface.

In the nonaqueous electrolyte secondary battery according to one embodiment of the present disclosure, it has been found that the formation of a low-resistance coating is promoted and low-temperature output characteristics are further enhanced by allowing the lithium transition metal oxide to contain tungsten (W). It is conceivable that mixing a tungsten oxide in the positive electrode mix layer and the presence of the tungsten oxide near the active material surface change the degradation state of the linear carboxylate to form a further low-resistance coating. This further enhances low-temperature output characteristics. In the nonaqueous electrolyte secondary battery according to one embodiment of the present disclosure, it is preferable that the lithium transition metal oxide contains W and the tungsten oxide is mixed in the positive electrode mix layer.

An example of an embodiment is described below in detail.

A nonaqueous electrolyte secondary battery that is an example of the embodiment includes a positive electrode including positive electrode mix layers, a negative electrode, and a nonaqueous electrolyte. A separator is preferably placed between the positive electrode and the negative electrode. The nonaqueous electrolyte secondary battery has, for example, a structure in which a wound electrode assembly prepared by winding the positive electrode and the negative electrode with the separator therebetween and the nonaqueous electrolyte are housed in an enclosure. Alternatively, a stacked electrode assembly prepared by alternately stacking positive electrodes and negative electrodes with separators therebetween or another type of electrode assembly may be used instead of the wound electrode assembly. The following cases can be exemplified as a battery case in which the electrode assembly and the nonaqueous electrolyte are housed: cylindrical, rectangular, coin-shaped, and button-shaped metal cases; cases (laminated batteries) formed from a laminated sheet prepared by laminating metal foil with a resin sheet; and the like.

[Positive Electrode]

The positive electrode is composed of, for example, a positive electrode current collector made of metal foil or the like and the positive electrode mix layers, which are placed on the positive electrode current collector. The positive electrode current collector used may be foil of a metal, such as aluminium, stable within the potential range of the positive electrode; a film including a surface layer containing the metal; or the like. The positive electrode mix layers contain a lithium transition metal oxide which is a positive electrode active material and a phosphate compound as an essential component and preferably further contain a tungsten oxide, a conductive material, and a binding material. The positive electrode can be prepared in such a manner that, for example, positive electrode mix slurry containing the positive electrode active material, the binding material, and the like is applied to the positive electrode current collector; wet coatings are dried; the dry coatings are pressed using a press machine; and the positive electrode mix layers are thereby famed on both surfaces of the current collector.

The lithium transition metal oxide is preferably an oxide represented by the formula $Li_{1+x}MaO_{2+b}$, (where x+a=1, $-0.2<x\leq0.2$, $-0.1\leq b\leq0.1$, and M is at least one metal element selected from the group consisting of Ni, Co, Mn, and Al). In particular, in the case of using a lithium transition metal oxide containing nickel (Ni), a good coating is likely to be famed by the degradation of a linear carboxylate. Therefore, M is preferably at least Ni. The lithium transition metal oxide preferably contains cobalt (Co) and manganese (Mn) in addition to Ni. The lithium transition metal oxide preferably contains aluminium (Al) instead of Mn in addition to Ni, Co, and Mn.

The proportion of Ni in the above M is preferably 30 mole percent or more. Ni is preferably contained in the form of $Ni^{3+}$. In the case of using a $Ni^{3+}$-containing lithium transition metal oxide, the formation of a good coating is promoted. The $Ni^{3+}$-containing lithium transition metal oxide is a lithium nickel-cobalt-manganate in which the molar ratio is Ni>Mn. The molar ratio of Ni to Co to Mn is, for example, 3:5:2, 4:3:3, 5:2:3, 5:3:2, 6:2:2, 7:1:2, 7:2:1, or 8:1:1. In a lithium nickel-cobalt-aluminate, the molar ratio of Ni to Co to Al is, for example, 80:15:5, 85:12:3, or 90:7:3.

The lithium transition metal oxide contains zirconium (Zr) as an essential component. As described above, containing Zr increases the reactivity between an active material and solvent molecules in the nonaqueous electrolyte, thereby enabling a good coating to be famed on the surface of the active material. The content of Zr is preferably 0.05 mole percent to 10 mole percent with respect to metal elements, excluding Li, in the lithium transition metal oxide, more preferably 0.1 mole percent to 5 mole percent, and particularly preferably 0.2 mole percent to 3 mole percent. When the content of Zr is within this range, good charge/discharge characteristics are maintained and the formation of a low-resistance coating on the active material surface can be promoted.

The lithium transition metal oxide preferably further contains tungsten (W). Containing W probably further promotes the formation of the low-resistance coating on the active material surface and further enhances low-temperature output characteristics. The content of W, as well as Zr, is preferably 0.05 mole percent to 10 mole percent with respect to the metal elements, excluding Li, in the lithium transition metal oxide, more preferably 0.1 mole percent to 5 mole percent, and particularly preferably 0.2 mole percent to 3 mole percent.

Zr can be contained in the oxide in such a manner that in the synthesis of the lithium transition metal oxide, for example, a composite oxide containing Ni, Co, Mn, and the like; a Li compound such as lithium carbonate; and Zr or a zirconium compound such as zirconium oxide are mixed together and are fired. W can be contained in the oxide in such a manner that in the synthesis of the lithium transition metal oxide, W or a tungsten component such as a tungsten oxide is mixed. Solid solutions of Zr and W can be famed in the lithium transition metal oxide in such a manner that in the synthesis of the lithium transition metal oxide, a composite oxide containing Ni, Co, Mn, and the like; Zr; and W are mixed together and are fired. Zr and W are preferably present in the lithium transition metal oxide in the form of a solid solution and may be deposited at interfaces between primary particles or on the surfaces of secondary particles in the form of an oxide or metal.

The lithium transition metal oxide may further contain an additive element. Examples of the additive element include transition metal elements other than Mn, Ni, and Co; alkali metal elements; alkaline-earth metal elements; group 12 elements; group 13 elements; and group 14 elements. In particular, the following elements can be exemplified: boron (B), magnesium (Mg), aluminium (Al), titanium (Ti), chromium (Cr), iron (Fe), copper (Cu), zinc (Zn), niobium (Nb), molybdenum (Mo), tantalum (Ta), tin (Sn), sodium (Na), potassium (K), barium (Ba), strontium (Sr), calcium (Ca), and the like.

The particle diameter of the lithium transition metal oxide is not particularly limited and is preferably 2 μm to 30 μm. Particles of the lithium transition metal oxide are secondary particles composed of primary particles, joined together, having a diameter of, for example, 50 nm to 10 μm. The particle diameter of the lithium transition metal oxide is the volume-average particle diameter determined by laser diffractometry. The BET specific surface area of the lithium transition metal oxide is not particularly limited and is preferably 0.1 $m^2$/g to 6 $m^2$/g. The BET specific surface area of the lithium transition metal oxide can be measured with a known BET powder specific surface area analyzer.

The phosphate compound probably contributes to reducing the resistance of a coating formed on the surface of the positive electrode active material by the degradation of the linear carboxylate as described above. The phosphate compound, which is mixed in the positive electrode mix layers, is at least one selected from the group consisting of, for example, lithium phosphate, lithium dihydrogen phosphate, cobalt phosphate, nickel phosphate, manganese phosphate, potassium phosphate, and ammonium dihydrogen phosphate. Among these compounds, lithium phosphate is particularly preferably used.

The content of the lithium phosphate is preferably 0.03 weight percent to 6 weight percent with respect to the total mass of the lithium transition metal oxide (positive electrode active material), more preferably 0.06 weight percent to 4.5 weight percent, and particularly preferably 0.3 weight percent to 3 weight percent. In terms of phosphorus (P), the content of the lithium phosphate is preferably 0.01 weight percent to 1.5 weight percent with respect to the total mass of the lithium transition metal oxide, more preferably 0.02 weight percent to 1.2 weight percent, and particularly preferably 0.1 weight percent to 1.0 weight percent. When the content of the lithium phosphate is within this range, the capacity of the positive electrode is maintained and the effect of foaming the low-resistance coating on the surface of the positive electrode active material can be sufficiently exhibited.

The particle diameter of the phosphate compound is preferably less than the particle diameter of the lithium transition metal oxide and is particularly preferably 25% or less of the particle diameter of the oxide. The particle diameter of the phosphate compound is, for example, 50 nm to 10 μm. When the particle diameter thereof is within this range, the dispersion state of the phosphate compound in the positive electrode mix layers is maintained good and the low-resistance coating is likely to be famed on the active material surface. Herein, the particle diameter of the phosphate compound is the value obtained in such a manner that 100 particles of the phosphate compound observed with a scanning electron microscope (SEM) are randomly extracted, the lengths of the major and minor axes of each particle are measured, and the measurements are averaged. When the phosphate compound is present in the form of aggregates, the particle diameter of the phosphate compound is the diameter of particles in the minimum units forming aggregates.

The tungsten oxide probably has a function for changing the degradation state of the linear carboxylate to form a further low-resistance coating as described above. The tungsten oxide, which is mixed in the positive electrode mix layers, is not particularly limited and is preferably $WO_3$, in which the oxidation number of tungsten is hexavalent and tungsten is most stable.

The content of the tungsten oxide is preferably 0.05 mole percent to 10 mole percent with respect to the metal elements, excluding Li, in the lithium transition metal oxide, more preferably 0.1 mole percent to 5 mole percent, and particularly preferably 0.2 mole percent to 3 mole percent. When the content of the tungsten oxide is within this range, good charge/discharge characteristics are maintained and the effect of changing the degradation state of the linear carboxylate to form a further low-resistance coating can be sufficiently exhibited.

The particle diameter of the tungsten oxide is preferably less than the particle diameter of the lithium transition metal oxide and is particularly preferably 25% or less of the particle diameter of the oxide. The particle diameter of the tungsten oxide is substantially the same as, for example, the particle diameter of the phosphate compound and is 50 nm to 10 μm. When the particle diameter thereof is within this range, the dispersion state of the tungsten oxide in the positive electrode mix layers is maintained good and the low-resistance coating is likely to be formed on the active material surface. The particle diameter of the tungsten oxide is the value determined by substantially the same method as that used to determine the particle diameter of the phosphate compound.

The phosphate compound and the tungsten oxide can be attached to the surfaces of particles of the active material by mechanically mixing the phosphate compound and the tungsten oxide with, for example, a lithium transition metal oxide (positive electrode active material) containing Zr or W. Alternatively, in a step of preparing the positive electrode mix slurry by kneading the conductive material and the binding material, the phosphate compound and the tungsten oxide may be mixed in the positive electrode mix layers by adding the phosphate compound and the tungsten oxide.

The conductive material is used to increase the electrical conductivity of the positive electrode mix layers. Examples of the conductive material include carbon materials such as carbon black, acetylene black, Ketjenblack, and graphite. These can be used alone or in combination.

The binding material is used to maintain the good contact between the positive electrode active material and the conductive material and to increase the adhesion of the positive electrode active material to the positive electrode current collector. Examples of the binding material include fluorinated resins such as polytetrafluoroethylene (PTFE) and polyvinylidene fluoride (PVdF), polyacrylonitrile (PAN), polyimide resins, acrylic resins, and polyolefin resins. These resins may be used in combination with carboxymethylcellulose (CMC), a salt thereof (that may be CMC-Na, CMC-K, CMC-NH$_4$, or a partially neutralized salt), polyethylene oxide (PEO), or the like. These may be used alone or in combination.

[Negative Electrode]

The negative electrode includes, for example, a negative electrode current collector made of metal foil or the like and negative electrode mix layers formed on the current collector. The negative electrode current collector used may be foil of a metal, such as copper, stable in the potential range of the negative electrode or a film including a surface layer made of the metal. The negative electrode mix layers preferably contain a negative electrode active material and a binding material. The negative electrode can be prepared in such a manner that, for example, negative electrode mix slurry containing the negative electrode active material, the binding material, and the like is applied to the negative electrode current collector; wet coatings are dried; the dry coatings are pressed using a roller; and the negative electrode mix layers are thereby famed on both surfaces of the current collector.

The negative electrode active material is not particularly limited and may be one capable of reversibly storing and releasing lithium ions. The following materials can be used: for example, a carbon material such as natural graphite or synthetic graphite; a metal, silicon (Si) or tin (Sn), alloying with lithium; an alloy containing these metal elements; a composite oxide; or the like. The negative electrode active material may be used alone or a mixture of multiple types of negative electrode active materials may be used.

As is the case with the positive electrode, the binding material used may be a fluorinated resin, PAN, a polyimide resin, an acrylic resin, a polyolefin resin, or the like. In the case of using an aqueous solvent to prepare the negative electrode mix slurry, the following material is preferably used: styrene-butadiene rubber (SBR), CMC, a salt thereof, polyacrylic acid (PAA), a salt thereof (that may be PAA-Na, PAA-K, or a partially neutralized salt), polyvinyl alcohol (PVA), or the like.

[Nonaqueous Electrolyte]

The nonaqueous electrolyte contains a nonaqueous solvent and an electrolyte salt dissolved in the nonaqueous solvent. The nonaqueous solvent contains the linear carboxylate as described above. The following solvents can be used for the nonaqueous solvent: for example, esters other than the linear carboxylate, ethers, nitriles, amides such as dimethylformamide, and mixtures of two or more of these solvents. A sulfo group-containing compound such as propanesultone may be used. The nonaqueous solvent may contain a halogen-substituted compound obtained by substituting hydrogen in at least one of these solvents with an atom of a halogen such as fluorine.

The nonaqueous linear carboxylate is not particularly limited and is preferably a linear carboxylate containing three to five carbon atoms. Examples thereof include methyl propionate, ethyl propionate, methyl acetate, ethyl acetate, and propyl acetate. Among these carboxylates, methyl propionate is particularly preferably used. The content of the linear carboxylate is preferably 3 volume percent to 30 volume percent with respect to the total volume of the nonaqueous solvent, which makes up the nonaqueous electrolyte. When the content of the linear carboxylate is within this range, a good coating is likely to be famed on the active material surface and good storage durability can be obtained.

Examples of the esters (other than the linear carboxylate) include cyclic carbonates such as ethylene carbonate (EC), propylene carbonate (PC), butylene carbonate, and vinylene carbonate; linear carbonates such as dimethyl carbonate (DMC), ethyl methyl carbonate (EMC), diethyl carbonate (DEC), methyl propyl carbonate, ethyl propyl carbonate, and methyl isopropyl carbonate; and cyclic carboxylates such as γ-butyrolactone (GBL) and γ-valerolactone (GVL).

Examples of the ethers include cyclic ethers such as 1,3-dioxolane, 4-methyl-1,3-dioxolane, tetrahydrofuran, 2-methyltetrahydrofuran, propylene oxide, 1,2-butylene oxide, 1,3-dioxane, 1,4-dioxane, 1,3,5-trioxane, furan, 2-methylfuran, 1,8-cineol, and crown ethers and linear ethers such as 1,2-dimethoxyethane, diethyl ether, dipropyl ether, diisopropyl ether, dibutyl ether, dihexyl ether, ethyl vinyl ether, butyl vinyl ether, methyl phenyl ether, ethyl phenyl ether, butyl phenyl ether, pentyl phenyl ether, methoxytoluene, benzyl ethyl ether, diphenyl ether, dibenzyl ether, o-dimethoxybenzene, 1,2-diethoxyethane, 1,2-dibutoxyethane, diethylene glycol dimethyl ether, diethylene glycol diethyl ether, diethylene glycol dibutyl ether, 1,1-dimethoxymethane, 1,1-diethoxyethane, triethylene glycol dimethyl ether, and tetraethylene glycol dimethyl.

Examples of the nitriles include acetonitrile, propionitrile, butyronitrile, valeronitrile, n-heptanenitrile, succinonitrile, glutaronitrile, adiponitrile, pimelonitrile, 1,2,3-propanetricarbonitrile, and 1,3,5-pentanetricarbonitrile.

The following carboxylate is preferably used as the halogen-substituted compound: a fluorinated cyclic carbonate such as fluoroethylene carbonate (FEC), a fluorinated linear carbonate, a fluorinated linear carboxylate such as methyl fluoropropionate (FMP), or the like.

A solvent mixture of the cyclic carbonate and the linear carbonate is preferably used as the nonaqueous solvent in addition to the linear carboxylate. The volume ratio between the cyclic carbonate and linear carbonate used in combination is preferably 2:8 to 5:5.

The electrolyte salt is preferably a lithium salt. Examples of the lithium salt include $LiBF_4$; $LiClO_4$; $LiPF_6$; $LiAsF_6$; $LiSbF_6$; $LiAlCl_4$; LiSCN; $LiCF_3SO_3$; $LiC(C_2F_5SO_2)$; $LiCF_3CO_2$; $Li(P(C_2O_4)F_4)$ $Li(P(C_2O_4)F_2)$ $LiPF_{6-x}$ $(C_nF_{2n+1})_x$ (where 1<x<6 and n is 1 or 2); $LiB_{10}Cl_{10}$; LiCl; LiBr; LiI; chloroborane lithium; lithium lower aliphatic carboxylates; borates such as $Li_2B_4O_7$, $Li(B(C_2O_4)_2)$ [lithium bis(oxalate) borate (LiBOB)], and $Li(B(C_2O_4)F_2)$; and imide salts such as $LiN(FSO_2)_2$ and $LiN(C_1F_{21+1}SO_2)$ $(C_mF_{2m+1}SO_2)$ {where 1 and m are integers greater than or equal to 1}. The lithium salt may be used alone or a mixture of multiple types of these salts may be used. Among these salts, at least one fluorine-containing lithium salt is preferably used from the viewpoint of ionic conductivity and electrochemical stability. For example, $LiPF_6$ is preferably used. In particular, from the viewpoint that a coating stable in a high-temperature environment is formed on a surface of the negative electrode, the fluorine-containing lithium salt and a lithium salt containing oxalato complex anions (for example, LiBOB) are preferably used in combination. The concentration of the lithium salt is preferably 0.8 mol to 1.8 mol per liter of the nonaqueous solvent.

[Separator]

The separator used is a porous sheet having ionic permeability and electrical insulation properties. Examples of the porous sheet include microporous thin films, fabrics, and nonwoven fabrics. The separator is preferably made of an olefin resin such as polyethylene or polypropylene or cellulose. The separator may be a laminate including a cellulose fiber layer and a thermoplastic resin fiber layer made of the olefin resin or the like. Alternatively, the separator may be a multilayer separator including a polyethylene layer and a polypropylene layer. A separator surface-coated with resin such as an aramid resin can be used.

A filler layer containing an inorganic filler may be placed at the interface between the separator and at least one of the positive electrode and the negative electrode. The inorganic filler is, for example, an oxide containing at least one of titanium, aluminium, silicon, and magnesium; a phosphate compound; or the like. The surface of filler may be treated with a hydroxide or the like. The filler layer can be formed in such a manner that, for example, slurry containing the filler is applied to a surface of the positive electrode, the negative electrode, or the separator. Alternatively, the filler layer may be formed in such a manner that a sheet containing the filler is separately prepared and is attached to a surface of the positive electrode, the negative electrode, or the separator.

EXAMPLES

The present disclosure is further described below in detail with reference to examples. The present disclosure is not limited to the example.

Experiment Example 1

[Preparation of Positive Electrode Active Material]

A hydroxide represented by $[Ni_{0.5}Co_{0.2}Mn_{0.3}](OH)_2$ was synthesized in such a manner that $NiSO_4$, $CoSO_4$, and $MnSO_4$ were mixed in an aqueous solution and were co-precipitated. The hydroxide was fired at 500° C., whereby a nickel-cobalt-manganese composite oxide was obtained. Next, the composite oxide, lithium carbonate, zirconium oxide ($ZrO_2$), and a tungsten oxide ($WO_3$) were mixed in an Ishikawa-type Raikai mortar. The mixing ratio (molar ratio) of the total amount of Ni, Co, and Mn to Li to Zr to W was 1:1.2:0.005:0.005. The mixture was fired at 900° C. for 20 hours, followed by crushing, whereby a lithium transition metal oxide (positive electrode active material), containing Zr and W, represented by $Li_{1.07}Ni_{0.465}Co_{0.186}Mn_{0.279}O_2$ was prepared. From the analysis of a cross section of a particle by energy dispersive X-ray spectroscopy (EDX), it is conceivable that Zr and W are present in the lithium transition metal oxide in the form of solid solutions. Next, the obtained lithium transition metal oxide was mixed with $WO_3$ and lithium phosphate ($Li_3PO_4$), the amount of $WO_3$ being 0.5 mole percent of the total amount of metal elements (transition metals), excluding Li, in the oxide, the amount of lithium phosphate being 2 weight percent of the total mass of the oxide, whereby a positive electrode active material containing $WO_3$ and $Li_3PO_4$ attached to the surfaces of particles was obtained. Incidentally, the particle diameter of $WO_3$ and that of $Li_3PO_4$ are 300 nm and 500 nm, respectively, as determined by the above-mentioned method.

[Preparation of Positive Electrode]

The positive electrode active material, carbon black, and polyvinylidene fluoride (PVDF) were mixed at a mass ratio of 92:5:3. N-methyl-2-pyrrolidone (NMP) serving as a dispersion medium was added to the mixture, followed by stirring using a mixer (T. K. HIVIS MIX, manufactured by PRIMIX Corporation), whereby positive electrode mix slurry was prepared. Subsequently, the positive electrode mix slurry was applied to aluminium foil that was a positive electrode current collector, wet coatings were dried, and the dry coatings were pressed with a roller. In this way, a positive electrode including positive electrode mix layers formed on both surfaces of the aluminium foil was prepared.

[Preparation of Negative Electrode]

A graphite powder, carboxymethylcellulose (CMC), and styrene-butadiene rubber (SBR) were mixed at a mass ratio of 98:1:1, followed by adding water. This was stirred using a mixer (T. K. HIVIS MIX, manufactured by PRIMIX Corporation), whereby negative electrode mix slurry was prepared. Next, the negative electrode mix slurry was applied to copper foil that was a negative electrode current collector, wet coatings were dried, and the dry coatings were pressed with a roller. In this way, a negative electrode including negative electrode mix layers famed on both surfaces of the copper foil was prepared.

[Preparation of Nonaqueous Electrolyte Solution]

Ethylene carbonate (EC), ethyl methyl carbonate (EMC), dimethyl carbonate (DMC), and methyl propionate (MP) were mixed at a volume ratio of 30:25:40:5. LiPF$_6$ was dissolved in the solvent mixture such that the concentration was 1 mol/L, followed by dissolving 0.5 weight percent of vinylene carbonate.

[Preparation of Battery]

An aluminium lead was attached to the positive electrode. A nickel lead was attached to the negative electrode. A microporous membrane made of polyethylene was used as a separator. The positive electrode and the negative electrode were spirally wound with the separator therebetween, whereby a wound electrode assembly was prepared. The electrode assembly was housed in a battery case body with a bottomed cylindrical shape. After the nonaqueous electrolyte solution was poured into the battery case body, an opening of the battery case body was sealed with a gasket and a sealing body, whereby a cylindrical nonaqueous electrolyte secondary battery (hereinafter referred to as Battery A1) was prepared.

Experiment Example 2

Battery B1 was prepared in substantially the same manner as that used in Experiment Example 1 except that no Li$_3$PO$_4$ was mixed with the lithium transition metal oxide prepared in Experiment Example 1 and a mixture of EC, EMC, and DMC mixed at a volume ratio of 30:30:40 was used as a solvent mixture of a nonaqueous electrolyte solution.

Experiment Example 3

Battery B2 was prepared in substantially the same manner as that used in Experiment Example 1 except that no Li$_3$PO$_4$ was mixed with the lithium transition metal oxide prepared in Experiment Example 1.

Experiment Example 4

Battery B3 was prepared in substantially the same manner as that used in Experiment Example 1 except that a mixture of EC, EMC, and DMC mixed at a volume ratio of 30:30:40 was used as a solvent mixture of a nonaqueous electrolyte solution.

[Evaluation of Low-Temperature Output Characteristics]

After the above-mentioned batteries were charged up to 50% of the rated capacity thereof, the maximum current dischargeable for 10 seconds at a battery temperature of −30° C. when the discharge cut-off voltage was 2.5 V was measured. The output at a state of charge (SOC) of 50% was determined by an equation below. Evaluation results of low-temperature output characteristics are shown in Table 1 in terms of relative values using the output of Battery B1 as a reference (100).

Output (SOC of 50%)=maximum current×discharge cut-off voltage (2.5 V)

The rated capacity of each battery was the discharge capacity that was determined in such a manner that the battery was charged to 4.1 V with a current of 800 mA under 25° C. conditions in a constant current mode, was charged with a voltage of 4.1 V in a constant voltage mode, and was then discharged to 2.5 V with a current of 800 mA in a constant current mode.

TABLE 1

| Battery | Positive electrode active material | | | Positive electrode mix mixture | | Electrolyte solution MP content (volume percent) | Output Relative value (percent) |
|---|---|---|---|---|---|---|---|
| | Lithium transition metal oxide | Zr content (mole percent) | W content (mole percent) | Li$_3$PO$_4$ (weight percent) | WO$_3$ (mole percent) | | |
| A1 | Li$_{1.07}$Ni$_{0.465}$Co$_{0.186}$Mn$_{0.279}$O$_2$ | 0.5 | 0.5 | 2 | 0.5 | 5 | 110 |
| B1 | Li$_{1.07}$Ni$_{0.465}$Co$_{0.186}$Mn$_{0.279}$O$_2$ | 0.5 | 0.5 | — | 0.5 | — | 100 |
| B2 | Li$_{1.07}$Ni$_{0.465}$Co$_{0.186}$Mn$_{0.279}$O$_2$ | 0.5 | 0.5 | — | 0.5 | 5 | 101 |
| B3 | Li$_{1.07}$Ni$_{0.465}$Co$_{0.186}$Mn$_{0.279}$O$_2$ | 0.5 | 0.5 | 2 | 0.5 | — | 100 |

As is clear from the results in Table 1, Battery A1, in which the lithium transition metal oxide (positive electrode active material) containing zirconium (Zr) and lithium phosphate are contained in the positive electrode mix layers and methyl propionate (MP) is contained in the electrolyte solution, is superior in low-temperature output characteristics to the other batteries. This result is probably because a low-resistance coating was formed on the surface of an active material and therefore reaction resistance on the active material surface was reduced. It is supposed that the low-resistance coating is formed on the active material surface, which has increased reactivity with molecules of a solvent (MP) because of containing Zr, by the action of lithium phosphate present near the surface. However, in the case where no Zr is contained in the lithium transition metal oxide, the case where no lithium phosphate is present in the positive electrode mix layers, or the case where no MP is present in the electrolyte solution (Batteries B1 to B3), no increases in low-temperature output characteristics are exhibited and it is conceivable that no low-resistance coating is famed the active material surface. That is, the low-resistance coating on the active material surface is formed only in the case where the lithium transition metal oxide contains Zr, a phosphate compound is present near the active material surface, and a linear carboxylate is contained in an electrolyte solution.

INDUSTRIAL APPLICABILITY

A nonaqueous electrolyte secondary battery that is an example of the above embodiment is suitable for, for example, power supplies for driving mobile data terminals such as mobile phones, notebook personal computers, smartphones, and tablet terminals and is particularly suitable for applications needing high energy density. Furthermore, the nonaqueous electrolyte secondary battery is conceivably used for high-output applications such as electric vehicles (EVs), hybrid electric vehicles (HEVs), and electric tools.

The invention claimed is:

1. A nonaqueous electrolyte secondary battery comprising:
   a positive electrode including a positive electrode mix layer, a negative electrode, and a nonaqueous electrolyte,
   wherein the positive electrode mix layer contains a lithium transition metal oxide containing zirconium (Zr) and also contains a phosphate compound and the nonaqueous electrolyte contains a linear carboxylate,
   wherein the phosphate compound is $Li_3PO_4$,
   wherein the positive electrode mix layer contains a tungsten oxide, and
   wherein an average particle diameter of the tungsten oxide determined by a scanning electron microscope is less than an average particle diameter of the $Li_3PO_4$ determined by the scanning electron microscope.

2. The nonaqueous electrolyte secondary battery according to claim 1, wherein the lithium transition metal oxide contains tungsten (W).

3. The nonaqueous electrolyte secondary battery according to claim 1, wherein the linear carboxylate is methyl propionate.

4. The nonaqueous electrolyte secondary battery according to claim 1, wherein the tungsten oxide is $WO_3$.

5. The nonaqueous electrolyte secondary battery according to claim 1, wherein the lithium transition metal oxide contains nickel (Ni), cobalt (Co), and manganese (Mn).

6. The nonaqueous electrolyte secondary battery according to claim 1, wherein the content of the linear carboxylate is 3 volume percent to 30 volume percent with respect to the total volume of a nonaqueous solvent making up the nonaqueous electrolyte.

7. The nonaqueous electrolyte secondary battery according to claim 1, wherein the diameter of the tungsten oxide and the diameter of the $Li_3PO_4$ are 50 nm to 10 μm.

8. The nonaqueous electrolyte secondary battery according to claim 1, wherein an amount of $Li_3PO_4$ relative to a total amount of the lithium transition metal oxide is larger than an amount of the tungsten oxide relative to the total amount of the lithium transition metal oxide.

9. The nonaqueous electrolyte secondary battery according to claim 8, wherein the amount of $Li_3PO_4$ relative to a total amount of the lithium transition metal oxide is from 0.03 wt % to 6 wt %.

10. The nonaqueous electrolyte secondary battery according to claim 8, wherein the amount of $Li_3PO_4$ relative to a total amount of the lithium transition metal oxide is from 0.03 wt % to 3 wt %.

11. A nonaqueous electrolyte secondary battery comprising:
    a positive electrode including a positive electrode mix layer, a negative electrode, and a nonaqueous electrolyte,
    wherein the positive electrode mix layer contains a lithium transition metal oxide containing zirconium (Zr) and also contains a phosphate compound and the nonaqueous electrolyte contains a linear carboxylate,
    wherein the phosphate compound is $Li_3PO_4$,
    wherein the content of the linear carboxylate is 3 volume percent to 30 volume percent with respect to the total volume of a nonaqueous solvent making up the nonaqueous electrolyte, and
    wherein the content of the linear carboxylate is 3 volume percent to 5 volume percent with respect to the total volume of a nonaqueous solvent in the nonaqueous electrolyte.

* * * * *